(12) United States Patent
Fischell

(10) Patent No.: US 8,206,359 B1
(45) Date of Patent: Jun. 26, 2012

(54) INTRODUCER SHEATH WITH ADHESIVE ATTACHMENT MEANS AND A ROTATING SIDE TUBE

(75) Inventor: Robert E. Fischell, Dayton, MD (US)

(73) Assignee: Fischell Innovations, Inc., Fairhaven, NJ (US)

( * ) Notice: Subject to any disclaimer, the term of this patent is extended or adjusted under 35 U.S.C. 154(b) by 0 days.

(21) Appl. No.: 13/164,829

(22) Filed: Jun. 21, 2011

(51) Int. Cl.
*A61M 5/178* (2006.01)
*A61M 5/32* (2006.01)

(52) U.S. Cl. .................. 604/167.01; 604/174

(58) Field of Classification Search .......... 604/171, 604/173–180, 164.01, 164.02, 165.01, 165.04, 604/167.01, 167.03, 167.05
See application file for complete search history.

(56) References Cited

U.S. PATENT DOCUMENTS

| 5,827,230 | A | 10/1998 | Bierman |
| 5,827,239 | A | 10/1998 | Dillon et al. |
| 5,944,697 | A * | 8/1999 | Biche ............... 604/174 |
| 2009/0234295 | A1 * | 9/2009 | Lampropoulos et al. ..... 604/174 |
| 2009/0306603 | A1 * | 12/2009 | Bierman et al. ............ 604/180 |

* cited by examiner

*Primary Examiner* — Kevin C Sirmons
*Assistant Examiner* — Andrew Gilbert
(74) *Attorney, Agent, or Firm* — Stoel Rives LLP

(57) ABSTRACT

The present invention is an introducer sheath that is improved by having an adhesive pad located near the sheath's proximal end that detachably attaches the introducer sheath to the patient's skin without requiring any additional parts that come from a separate sterile package such as a needle and a suture or a separate adhesive pad. The present invention also teaches a means to rotatingly connect the adhesive pad to the sheath's hemostasis valve so that the proximal portion of the hemostasis valve is free to rotate about the adhesive pad even after the adhesive pad is firmly attached to the patient's skin. This design allows the operator to position the side tube that is connected to the hemostasis valve at an optimum location relative to the patient's skin.

7 Claims, 2 Drawing Sheets

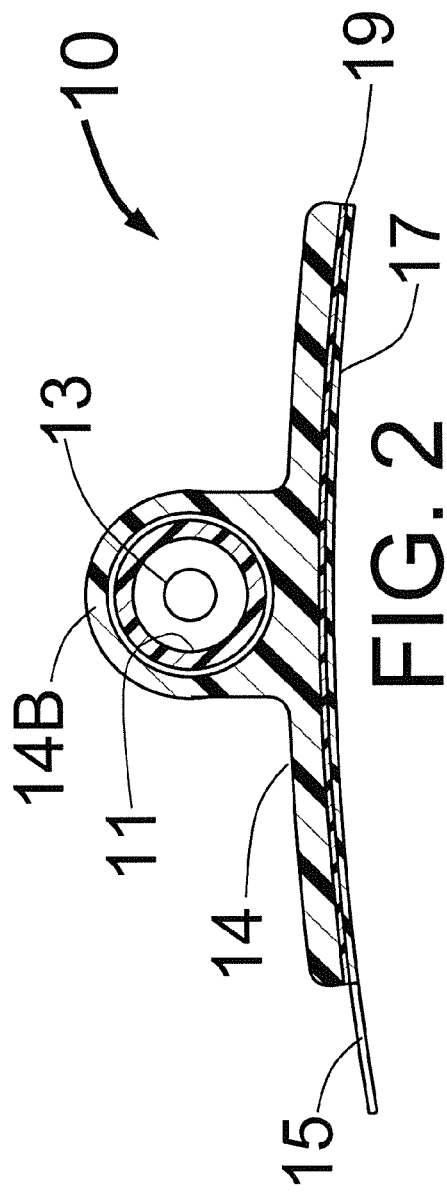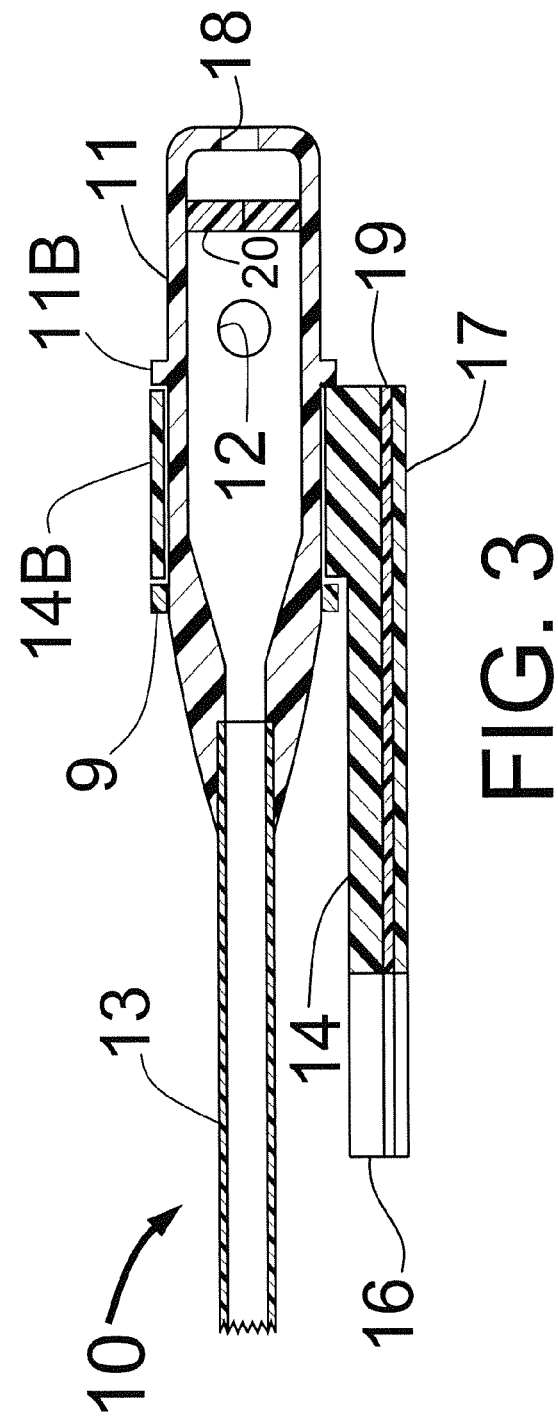

INTRODUCER SHEATH WITH ADHESIVE ATTACHMENT MEANS AND A ROTATING SIDE TUBE

FIELD OF THE INVENTION

This invention is in the field of devices to assist in the placement of catheters through the skin to treat certain coronary and peripheral vascular disorders.

BACKGROUND OF THE INVENTION

At the present time, physicians place an introducer sheath through the skin of a patient to access that patient's vascular system. Two usual places to gain access are through the skin at the groin to enter the femoral artery and through the skin in the wrist to access the radial artery. After the introducer sheath is placed through the skin, the physician will typically use a suture to fasten the proximal end of the introducer sheath to the patient's skin. That process requires the opening of an additional package that contains the suture thread and a needle, and also requires skin penetration that can be somewhat painful for the patient and has the possibility of infection.

In U.S. Pat. No. 5,827,239, S. F. Bierman has shown an adhesive attachment to the skin onto which certain catheters could be connected. One disadvantage of Bierman's attachment means is that it requires a separate sterile package to be opened in addition to the sterile package containing the introducer sheath. This requires additional procedure time and the separate sterilization of two different packages which increases costs. Another disadvantage of the Bierman device is that it is not as secure a holding means for a hemostasis valve as would be achieved if the adhesive attachment means was joined to the hemostasis valve of the introducer sheath. A highly reliable and rapid attachment means to secure the proximal end of the introducer sheath to the patient's skin would be an important improvement in the design of introducer sheaths.

Most of the introducer sheaths in use at this time have their side tube in a fixed position relative to the sheath's hemostasis valve. This is sometimes disadvantageous since the physician may wish for the side arm to be rotated to an alternate position. As described by J. E. Biche in U.S. Pat. No. 5,944,697, the prior art teaches a sheath design with a suture ring that can rotate relative to the sheath's hemostasis valve. However, as described above, there are certain disadvantages for an introducer sheath that that must be attached to the skin by means of a suture. What has not yet been available for the interventional cardiologist is the unique combination of an adhesive attachment means to attach the sheath's hemostasis valve to the patient's skin combined with a means to rotate the sheath's side tube relative to the adhesive connection means.

SUMMARY OF THE INVENTION

A key feature of the present invention is a novel attachment means located at a proximal section of the sheath. This attachment means is designed to facilitate rapid attachment and detachment of the proximal end of the sheath to the patient's skin. One embodiment of the present invention is an introducer sheath that is improved by having an adhesive pad located at or near the sheath's proximal end that detachably attaches the introducer sheath to the patient's skin without requiring any additional parts that come from a separate sterile package such as a needle and a suture or a separate adhesive pad. Specifically, one embodiment of the present invention is a flexible adhesive pad that is used to attach the sheath's hemostasis valve to the patient's skin. The adhesive pad utilizes a pressure sensitive adhesive on one side covered by a removable cover sheet which is removed to expose the pressure sensitive adhesive surface of the adhesive pad to quickly attach the introducer sheath to the skin. Either before or after the shaft of the introducer sheath is placed through the skin, the thin plastic (or paper) cover sheet that covers the pressure sensitive adhesive is removed. When the introducer sheath is then advanced into the target blood vessel to its fully inserted position, and the plastic cover sheet of the adhesive pad has been removed, the pressure sensitive adhesive pad is pushed firmly against the skin thereby firmly attaching the sheath to the patient's skin without requiring a sutured connection.

The use of a suture is now the conventional means that is used to make the attachment of the proximal end of an introducer sheath to the skin. The present invention eliminates the extra time required to open a separate package containing the needle and suture material, and the time required to place the suture through the introducer sheath and into the skin. The present invention also eliminates the penetration of the skin that can be somewhat uncomfortable for the patient and increases the possibility of infection. Still further, the cost of the needle and suture in a sterile pack is avoided. It is believed that suturing for retention of the sheath requires about 2 minutes of time for the operator. As a comparison, removing a plastic sheet cover from a pressure sensitive adhesive attachment to the sheath's proximal end and pushing the pressure sensitive adhesive against the skin could probably be accomplished in only 2-3 seconds. Furthermore, removing the suture could again take about 2 minutes compared to removing the pressure sensitive adhesive pad that would probably take less than 2 seconds to accomplish. Such time saving and ease of use is appreciated by those physicians who perform this procedure.

If a separate adhesive pad is used to attach an introducer sheath to the patient's skin, this requires additional time to open the sterile package and to place it in proper position on the skin before the introducer sheath is placed with its shaft into the patient's vascular system. The most accurate position for the introducer sheath is not guaranteed as is the case when the adhesive pad is rotatingly attached with the hemostasis valve. Also, using a separate adhesive pad there is always the possibility that the hemostasis valve will slip off of the pad when there is a considerable force exerted on the separate pad when a catheter is pushed into or pulled out of the hemostasis valve. Thus, there are many advantages to having a flexible adhesive pad that is attached to the hemostasis valve which hemostasis valve is part of the introducer sheath.

When an interventional cardiologist inserts an introducer sheath into a patient's vascular system, he desires to place the side tube that is connected to the sheath's hemostasis valve at an optimum position for injecting medications into the patient's vascular system. The present invention teaches a means to rotatingly connect the adhesive pad to the sheath's hemostasis valve so that the proximal portion of the hemostasis valve is free to rotate about the adhesive pad even after the adhesive pad is firmly attached to the patient's skin. This design allows the operator (the person performing the procedure) to position the side tube at an optimum location relative to the patient's skin. It should be understood that the "operator" could a cath lab technician, a nurse or a physician.

Thus one object of the present invention is to provide a means to secure the proximal end of an introducer sheath to a patient's skin without the use of a suture or a separate adhesive pad, this means being a flexible adhesive pad that is rotatingly attached to the hemostasis valve that is located at a proximal region of the introducer sheath.

Another object of this invention is to secure the proximal end of an introducer sheath to the skin without using a needle and suture so as to eliminate the discomfort that may be felt by the patient when a needle is used to penetrate his or her skin.

Still another object of this invention is to have a sufficient length of the hemostasis valve lying proximal to the proximal end of the adhesive pad so that it is easily gripped by the doctor who inserts the introducer sheath into the patient's vascular system.

Still another object of this invention is to have a hemostasis valve and its side tube that are free to rotate about the adhesive pad even after that adhesive pad is firmly attached to the patient's skin.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 2 is a cross section at "A-A" of FIG. 1 showing the construction of the adhesive pad and the hemostasis valve.

FIG. 3 is a cross section at "B-B" of FIG. 1 showing the construction of the adhesive pad and the hemostasis valve.

DETAILED DESCRIPTION OF THE INVENTION

Figure 1:
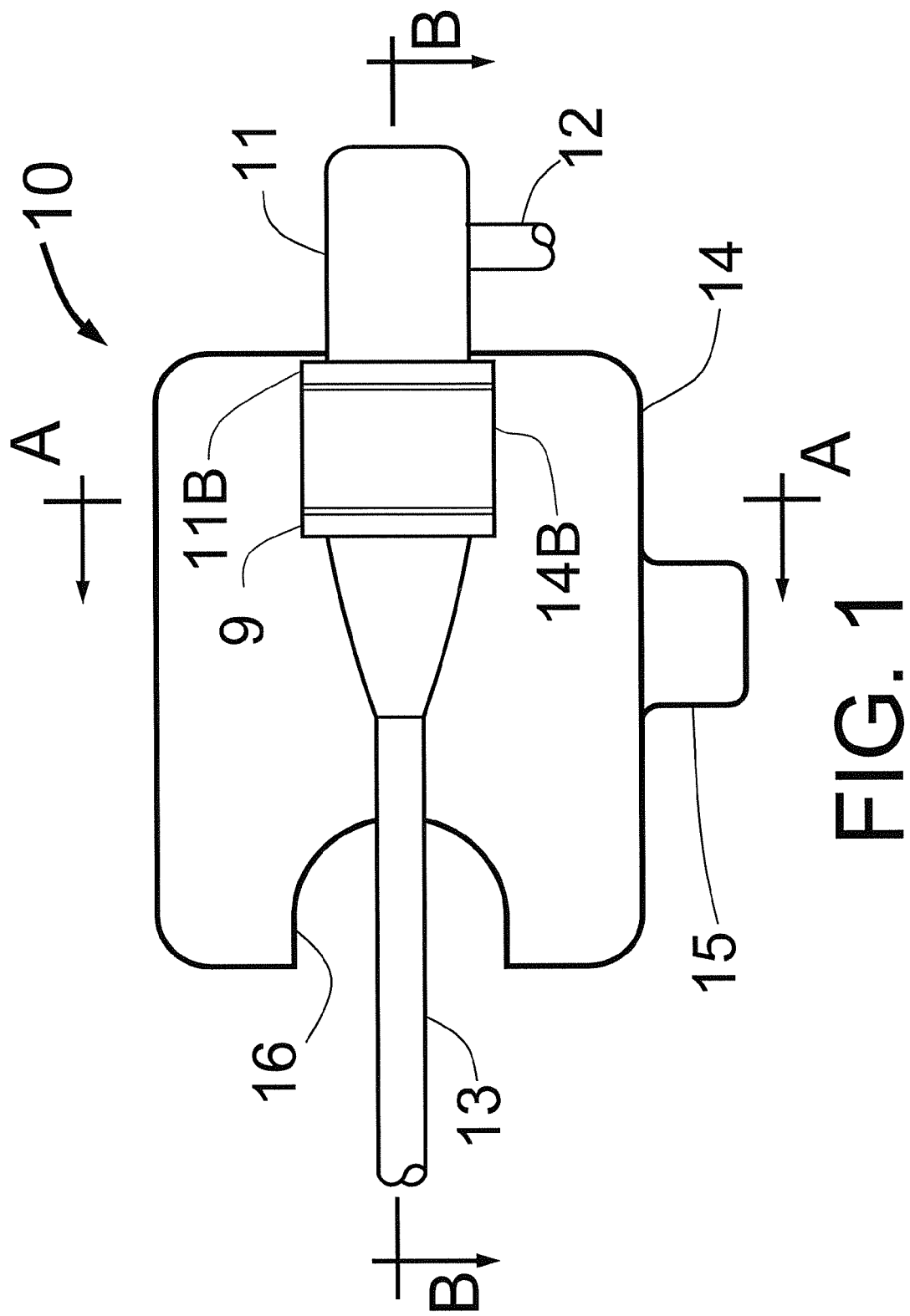
FIG. 1 is a top view of a preferred embodiment of the present invention wherein the adhesive pad is rotatingly attached to the hemostasis valve of the introducer sheath.

FIG. 1 is a top view of the present invention showing a proximal portion of an introducer sheath 10 that has a hemostasis valve 11 located at the sheath's proximal end. The hemostasis valve 11 has a side tube 12 that is used to flush the sheath with normal saline solution and to inject various medications as needed to treat the patient. At the distal end of the hemostasis valve 11 is the shaft 13 that is placed into the patient's vascular system for introducing various catheters. The flexible adhesive pad 14 has a cylindrical portion 14B within which the hemostasis valve 11 and its attached side tube 12 are free to rotate. The shoulder 11B of the hemostasis valve 11 and the slip-on-ring 9 surround the cylindrical portion 14B of the adhesive pad 14 to prevent that cylindrical portion 14B from coming off of the hemostasis valve 11. The adhesive pad 14, has a thin layer of pressure sensitive adhesive 19 as shown in FIGS. 2 and 3. As shown in FIGS. 1, 2 and 3, the tab 15 is used to remove a thin plastic covering 17 from the adhesive layer 19 immediately before the flexible pad 14 is pushed against the skin to secure the introducer sheath 10 to the patient's skin. It should also be understood that a suture ring (not shown) could be attached to the hemostasis valve 11. With such a suture ring, an interventional cardiologist (or any other operator) could make a suture attachment of the hemostasis valve 11 if it is decided to increase the holding power of the hemostasis valve 11 onto the patient's skin.

One important feature of this invention is the distal opening 16 that is made at the distal end of the pad 14 to allow easy passage of the shaft 13 into and through the patient's skin. This opening 16 allows the passage of the shaft 13 into the patient's skin at a place that is much closer to the hemostasis valve 11 which is a desirable attribute of this introducer sheath 10. A second important feature of this invention is the juxtaposition of the hemostasis valve 11 and the pad 14. Specifically, a reasonable length of the hemostasis valve 11 is situated proximal to the proximal end of the pad 14 so that it can be easily grasped by the interventional cardiologist for readily inserting the shaft 13 through the patient's skin.

FIG. 2 is a cross section of the introducer sheath 10 at section A-A of FIG. 1 showing the hemostasis valve 11 enclosed within the cylindrical portion 14B of the flexible pad 14, the interior lumen of the shaft 13, the flexible pad 14 onto which is attached the adhesive 19 covered by the removable plastic sheet 17. The tab 15 is used to remove the plastic sheet 17 from the adhesive layer 19 immediately prior to having the operator push the pad 14 against the patient's skin to secure the proximal portion of the introducer sheath 10 to the patient's skin. When the time has come to remove the adhesive pad 14 from the patient's skin, the operator can pull on the proximal portion of the hemostasis valve 11 to accomplish that removal. A separate tab to pull the adhesive pad 14 off of the patient's skin could be used but that is not really required.

FIG. 3 is a cross section of the introducer sheath 10 at section B-B of FIG. 1. This cross section clearly shows how the cylindrical portion 14B of the pad 14 is rotatingly joined to the hemostasis valve 11. The shoulder 11B is shown as it is formed as part of the shell of the hemostasis valve 11. The slip-on-ring 9 can be separately formed and then attached to the hemostasis valve 11 so as to hold the cylindrical portion 14B of the adhesive pad 14 in place. FIG. 3 also shows the interior lumen of the tube 12, the shaft 13 and the flexible pad 14 that has a layer of pressure sensitive adhesive 19 covered by a removable plastic sheet 17. FIG. 3 also shows the entry port 18 in the shell of the hemostasis valve 11 and the diaphragm 20 whose function is to eliminate outward blood flow through the port 18 whether or not a catheter (not shown) is placed through the hemostasis valve 11.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. An introducer sheath for placement of a tubular shaft into the vascular system of a human subject, the introducer sheath having a tubular shaft and a side tube that is fixedly attached to a shell of a hemostasis valve that is situated at a proximal portion of the introducer sheath, the introducer sheath having an adhesive pad that is designed to readily attach and detach a proximal portion of the introducer sheath to and from the skin of the human subject, the adhesive pad having a cylindrical holder into which is placed a cylindrical outer section of the shell of the hemostasis valve thus allowing the shell of the hemostasis valve to freely rotate within this cylindrical holder of the adhesive pad so that the side tube that is fixedly attached to the shell of the hemostasis valve can be rotated into any position that is desired by the operator as he inserts the introducer sheath into the patient's vascular system, the shell of the hemostasis valve having a shoulder formed on its outer surface at a first position thereof, and a ring member fixedly attached around the shell of the hemostasis valve at a second position on the outer surface of the shell of the hemostasis valve, the cylindrical holder of the adhesive pad being contained between the shoulder and the ring member, the shoulder and the ring member being placed so as to prevent the adhesive pad from sliding off the shell of the hemostasis valve while allowing rotation of the shell of the hemostasis valve with respect to the adhesive pad.

2. The introducer sheath of claim 1 where a distal portion of the adhesive pad is partially cut out so as to allow easier passage of the sheath's tubular shaft into the patient's skin.

3. The introducer sheath of claim 1 where a proximal portion of the shell of the hemostasis valve lies at least one centimeter proximal to the proximal end of the adhesive pad so that this proximal portion of the shell of the hemostasis valve can be held by the operator for placement of the introducer sheath into the patient's vascular system.

4. The introducer sheath of claim 1 where the adhesive pad has a thin plastic covering with a tab extending outward from the adhesive pad which tab can be pulled by the operator to remove the plastic covering from the adhesive pad prior to attaching the adhesive pad to the patient's skin.

5. The introducer sheath of claim 1 where the shoulder is located at a proximal portion of the shell of the hemostasis valve and the ring member is located at a distal portion of the shell of the hemostasis valve.

6. The introducer sheath of claim 1 where the shoulder is located at a proximal end of the adhesive pad such that the shoulder abuts the proximal end of the adhesive pad.

7. The introducer sheath of claim 1 further comprising a diaphragm, where the diaphragm is located proximal a proximal end of the adhesive pad.

\* \* \* \* \*